US009423325B2

(12) United States Patent
Enomoto et al.

(10) Patent No.: US 9,423,325 B2
(45) Date of Patent: Aug. 23, 2016

(54) BLOCK STORAGE DEVICE AND AUTOMATIC THIN-CUTTING DEVICE

(71) Applicant: SAKURA FINETEK JAPAN CO., LTD., Tokyo (JP)

(72) Inventors: Jyunya Enomoto, Tokyo (JP); Seigo Murakami, Tokyo (JP); Nobuyuki Nakagawa, Tokyo (JP)

(73) Assignee: SAKURA FINETEK JAPAN CO., LTD., Tokyo (JP)

( * ) Notice: Subject to any disclaimer, the term of this patent is extended or adjusted under 35 U.S.C. 154(b) by 0 days.

(21) Appl. No.: 14/440,210

(22) PCT Filed: Nov. 5, 2013

(86) PCT No.: PCT/JP2013/079903
§ 371 (c)(1),
(2) Date: May 1, 2015

(87) PCT Pub. No.: WO2014/073533
PCT Pub. Date: May 15, 2014

(65) Prior Publication Data
US 2015/0292992 A1    Oct. 15, 2015

(30) Foreign Application Priority Data

Nov. 8, 2012   (JP) .................................. 2012-246334

(51) Int. Cl.
| | |
|---|---|
| *A61B 10/00* | (2006.01) |
| *G01N 1/36* | (2006.01) |
| *G01N 1/06* | (2006.01) |
| *G01N 1/31* | (2006.01) |

(52) U.S. Cl.
CPC .. *G01N 1/36* (2013.01); *G01N 1/06* (2013.01); *G01N 1/312* (2013.01)

(58) Field of Classification Search
CPC ............................ G01N 2201/00; A61B 10/00
See application file for complete search history.

(56) References Cited

U.S. PATENT DOCUMENTS

| | | | |
|---|---|---|---|
| 5,386,318 A | 1/1995 | Kuehnert et al. | |
| 2009/0087904 A1* | 4/2009 | Heid ..................... | G01N 1/312 435/307.1 |
| 2010/0030364 A1 | 2/2010 | Fujimoto et al. | |
| 2010/0279342 A1 | 11/2010 | Kijima et al. | |

FOREIGN PATENT DOCUMENTS

| | | |
|---|---|---|
| CN | 1991330 | 7/2007 |
| JP | 2007-212386 | 8/2007 |
| JP | 2008-164521 | 7/2008 |
| JP | 4548356 | 7/2010 |
| JP | 2010-266394 | 11/2010 |
| WO | 01/42796 | 6/2001 |

OTHER PUBLICATIONS

International Search Report from corresponding PCT Application No. PCT/JP2013/079903 dated Dec. 3, 2013. English translation attached.
Office Action from related Chinese Application No. 201380057731.3 dated May 19, 2016. Partial English translation attached.
Extended European Search Report from related EPO Application No. 13852556.3 dated Jun. 6, 2016.

* cited by examiner

*Primary Examiner* — Jyoti Nagpaul
(74) *Attorney, Agent, or Firm* — Grossman, Tucker, Perreault & Pfelger, PLLC

(57) ABSTRACT

A block storage device includes: a magazine which accommodates embedding blocks to be inserted into or removed from the magazine in a state where the embedding blocks held in a cassette to which ID data is attached are arranged vertically in one row; a magazine holding portion which detachably holds each of the magazines; and a reading portion which reads the ID data. The magazine holding portion includes a rotary body which is rotatable around a rotation axis O, a holding mechanism which is multiply provided on a circumferential wall portion in the rotary body and detachably holds the magazines individually, and a rotation drive portion which positions one of the magazines at a block extraction position facing the reading portion by rotating the rotary body, and the magazine positioned at the block extraction position and the reading portion are movable relative to each other along the vertical direction.

5 Claims, 9 Drawing Sheets

BLOCK STORAGE DEVICE AND AUTOMATIC THIN-CUTTING DEVICE

TECHNICAL FIELD

The present invention relates to a block storage device which stores an embedding block, in which a biological sample is embedded, to be inserted into or removed from the block storage device, and an automatic thin-cutting device.

Priority is claimed on Japanese Patent Application No. 2012-246334, filed Nov. 8, 2012, the content of which is incorporated herein by reference.

BACKGROUND ART

As one method for inspecting and observing a biological sample extracted from a human body, a laboratory animal, or the like, a method is known in which a thin section is prepared from an embedding block in which the biological sample is embedded by an embedding agent, dye processing is performed on the thin section, and thus, the biological sample is observed.

In the related art, an operation of preparing the thin section is performed manually by an experienced operator using a sharp and thin cutting blade. However, in recent years, an automatic thin-cutting device capable of automatically performing the operation of preparing the thin section has begun to be provided. According to this automatic thin-cutting device, it is possible to continuously prepare the thin section without imposing a burden on the operator.

In addition, in the automatic thin-cutting device, quality management or the like is performed by reading ID data printed on a cassette to which the embedding block is fixed. For example, the ID data includes data which indicates an identification number for identifying the embedding blocks individually or data of the embedding block (data indicates that the biological sample is obtained from which experimental animal, data indicates that the biological sample is obtained from which internal organ of the experimental animal, or the like).

Accordingly, by reading the ID data, it is possible to correctly distinguish each of the plurality of embedding blocks, it is possible to correctly understand whether or not the thin-cutting ends, and as a result, it is possible to perform the quality management as described above.

CITATION LIST

Patent Literature

[Patent Document 1] Japanese Patent No. 4548356

SUMMARY OF INVENTION

Technical Problem

As a method which sets a plurality of embedding blocks in an automatic thin-cutting device, for example, a method in which cassettes are installed in a block storage portion in the device in a state where the cassettes in which the embedding blocks are placed on a divided planar plate are arranged, a method in which the embedding blocks are accommodated in a magazine capable of setting the embedding blocks in a state where the embedding blocks are arranged in a vertical multistage, and the magazine is installed in a block storage portion in the device, or the like is known.

In any case, an operation is performed in which the embedding block selected by a robot hand or the like is extracted from the block storage portion, and thereafter, the extracted embedding block is transported to an ID reading point, and the embedding block is returned again to the block storage portion after the reading of the ID data printed to the cassette ends (after the thin-cutting ends, if necessary).

Accordingly, for example, even when only the reading operation of the ID data is performed, it is necessary to transport the embedding block from the block storage portion to the ID reading point, and thus, throughput decreases. Particularly, the throughput is remarkably decreased when the transport distance from the block storage portion to the ID reading point is greater.

In addition, there is a need for a user to understand the ID data of the plurality of embedding blocks stored in the block storage portion before the thin-cutting operation is performed. However, in this case, it is necessary to repeat an operation in which each of the embedding blocks is extracted from the block storage portion and is transported to the ID reading point, and after the ID data is read, the embedding block is returned to the block storage portion, and thus, a lot of time is required.

Moreover, from the viewpoint of convenience, it is preferable to freely extract the embedding block, in which the thin-cutting is completed, from the device at an arbitrary timing without temporarily stopping the device, or to replace the embedding block with a new embedding block. However, the above-described matters cannot be easily performed in the related art. That is, since the robot hand or the like frequently accesses the block storage portion and is operated, from the viewpoint of safety, it is necessary to temporarily stop the device during the recovery and replacement of the embedding block.

Accordingly, whenever the recovery and replacement of the embedding block is performed, since it is necessary to repeatedly stop and start the device, a lot of time is required, and throughput decreases.

An aspect of the present invention is made in consideration of the above-described circumstances, and an object thereof is to provide a block storage device capable of effectively reading ID data attached to a plurality of stored embedding blocks and extracting an embedding block, in which thin-cutting is completed, at an arbitrary timing, and an automatic thin-cutting device having the block storage device.

Solution to Problem

In order to achieve the object, an aspect according to the present invention adopts the following configurations.

(1) According to an aspect of the present invention, there is provided a block storage device that stores an embedding block which includes an embedded biological sample and is held in a cassette to which ID data is attached in advance, the device including: a magazine configured to accommodate a plurality of the embedding blocks to be inserted into or removed from the magazine and to accommodate the embedding blocks in a state where the embedding blocks are arranged along a vertical direction in one row; a magazine holding portion configured to detachably hold each of a plurality of the magazines; and a reading portion configured to be disposed to be adjacent to the magazine holding portion and to read the ID data, wherein the magazine holding portion includes: a rotary body configured to be rotatable around a rotation axis extended in a vertical direction; a holding mechanism configured to be multiply provided at intervals along a circumferential direction on a circumferential wall portion in the rotary body and to detachably hold the plurality of the magazines; and a rotation drive portion configured to move the plurality of the magazines held by the holding mechanism in the circumferential direction by rotating the rotary body and to position one of the magazines at a block extraction position facing the reading portion, and the magazine positioned at the block extraction position and the reading portion are movable relative to each other along the vertical direction.

According to the aspect (1), it is possible to move the plurality of magazines held by the holding mechanism in the circumferential direction by rotating the rotary body by the rotation drive portion, and it is possible to set one of the magazines at the block extraction position. In addition, since the magazine set at the block extraction position and the reading portion are movable relative to each other along the vertical direction, it is possible to rapidly read the ID data attached to each cassette of the plurality of embedding blocks which are arranged in one row along the vertical direction in the magazine.

In this way, in the state where the embedding blocks are accommodated in the magazine, it is possible to effectively read the ID data of all the embedding blocks in the magazine.

Moreover, it is possible to remove the magazines, which are positioned at positions except for the block extraction position, from the holding mechanism at an arbitrary timing by stopping the rotary body, and thus, it is possible to appropriately perform the recovery, the replacement, or the like of the embedding block accommodated in the magazine. In addition, during this, for example, it is possible to perform a thin-cutting operation on the embedding block accommodated in the magazine set at the block extraction position without being affected by the recovery, the replacement, or the like.

(2) In the aspect (1), a plurality of the holding mechanisms may be movable in the vertical direction with respect to the rotary body, and the magazine holding portion may include: a lifting mechanism configured to vertically move the holding mechanism which holds the magazine positioned at the block extraction position, among the plurality of the holding mechanisms; and a regulation mechanism configured to regulate movements in the vertical direction of the remaining holding mechanisms which hold the magazines except for the magazine positioned at the block extraction position, among the plurality of the holding mechanisms.

In this case, after the magazine is set at the block extraction position by the rotation of the rotary body, it is possible to move only the holding mechanism, which holds the magazine, in the vertical direction. Accordingly, even in the state where the reading portion is fixed, it is possible to read the ID data of the embedding block in the magazine which is set at the block extraction position.

(3) In the aspect (1) or (2), the block storage device may further include a protection cover configured to cover the periphery of the circumferential wall portion in the rotary body, and an opening portion accessible to the magazine except for the magazine positioned at the block extraction position among the plurality of the magazines may be formed on the protection cover.

In this case, since the periphery of the rotary body is covered by the protection cover, it is possible to prevent the rotary body from coming into contact with the outside, and safety is obtained. In addition, when the magazine positioned at the position except for the block extraction position is removed from the holding mechanism at an arbitrary timing, it is possible to reliably perform the removal using the opening portion which is formed on the protection cover.

(4) In any one of aspects (1) to (3), the block storage device may further include a control portion configured to perform thin-cutting management of the embedding block based on the ID data read by the reading portion, and when the control portion determines that the thin-cutting is completed with respect to all of the plurality of the embedding blocks accommodated in the magazine, the control portion may inform of the fact.

In this case, when the magazine positioned at the position except for the block extraction position is removed from the holding mechanism at an arbitrary timing, it is possible to prevent the magazine from being removed in a state where the embedding block which is not thinly cut remains.

(5) According to another aspect of the present invention, there is provided an automatic thin-cutting device, including: the block storage device according to any one of aspects (1) to (4); a block transport mechanism configured to insert or remove one embedding block which is selected from the embedding blocks accommodated in the magazine positioned at the block extraction position into or from the magazine and to transport the embedding block to a thin-cutting position; a thin-cutting mechanism configured to perform the thin-cutting on the embedding block set at the thin-cutting position and to cut a thin section; and a housing configured to accommodate the components.

According to the aspect (5), since the automatic thin-cutting device includes the above-described block storage device, it is possible to rapidly understand the ID data before the thin-cutting is performed, and it is possible to effectively perform the thin-cutting operation of a desired embedding block. Moreover, since components are accommodated inside the housing, the components are not easily affected by dust or the like, and thus, it is possible to prepare the thin section having high quality.

Advantageous Effects of Invention

According to aspects of the present invention, it is possible to effectively read ID data attached to a plurality of stored embedding blocks, and it is possible to extract an embedding block, in which thin-cutting is completed, at an arbitrary timing.

DESCRIPTION OF EMBODIMENTS

Hereinafter, an embodiment of the present invention will be described with reference to the drawings.

<Configuration of Automatic Thin-Cutting Device>

Figure 1:
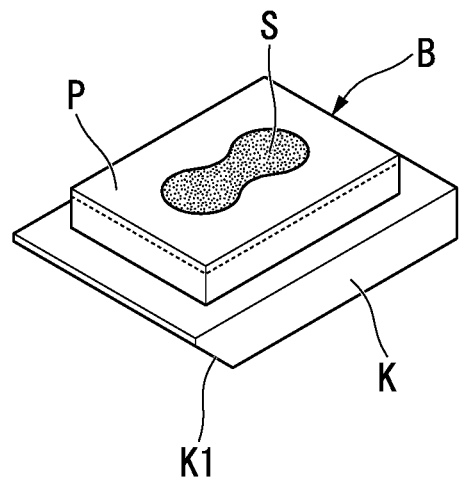
FIG. 1 is a perspective view of an embedding block and a cassette which are used by an automatic thin-cutting device according to the present invention.
Figure 2:
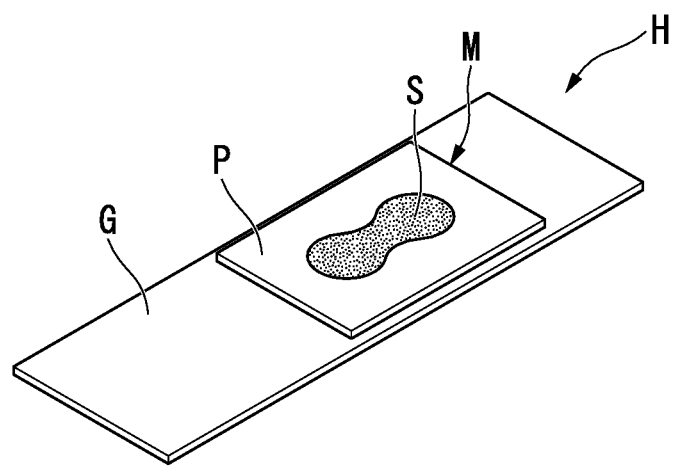
FIG. 2 is a perspective view showing a state where a thin section thinly cut from the embedding block shown in FIG. 1 is fixed to a slide glass and a thin section sample is made.

As shown in FIG. 1, an automatic thin-cutting device 1 of the present embodiment is a device which thinly cuts an embedding block B, in which a biological sample S is embedded by paraffin P serving as an embedding material, to a thickness of 3 μm to 5 μm, for example. Accordingly, it is possible to prepare a thin section M shown in FIG. 2 by the automatic thin-cutting device 1.

In addition, the automatic thin-cutting device 1 of the present embodiment not only can prepare the thin section M but also can automatically perform an operation of accommodating the thin section samples H in a basket after transferring the thin section M to the substrate such as a slide glass G and preparing the thin section samples H.

In addition, the embedding block B is a rectangular block in a plan view in which moisture in the formalin-fixed biological sample S is paraffin-substituted, and thereafter, the periphery is hardened in a block shape by the paraffin P. Accordingly, the biological sample S is embedded in the paraffin P. In addition, for example, the biological sample S is a tissue such as an internal organ extracted from a human body, experimental animal, or the like, and is a tissue which is appropriately selected in a medical field, a pharmaceutical field, the food industry, a biological field, or the like.

In addition, as shown in FIG. 1, the embedding block B is fixed to a cassette K.

The cassette K is formed in a box shape by a resin having chemical resistance or the like, and has a role as a fixing table which fixes the embedding block B. One side surface of the cassette K is an inclined surface K1 in which the surface faces downward. ID data (not shown), which includes a production number of the cassette K, a preparation date of the embedding block B, various data of the biological sample S, or the like, is recorded on the inclined surface K1. Accordingly, it is possible to manage quality of the embedding block B by reading the ID data.

Subsequently, each component of the automatic thin-cutting device will be described.

In the present embodiment, first, the components configuring the automatic thin-cutting device are sequentially and simply described, and thereafter, the necessary components are described in detail.

Figure 3:
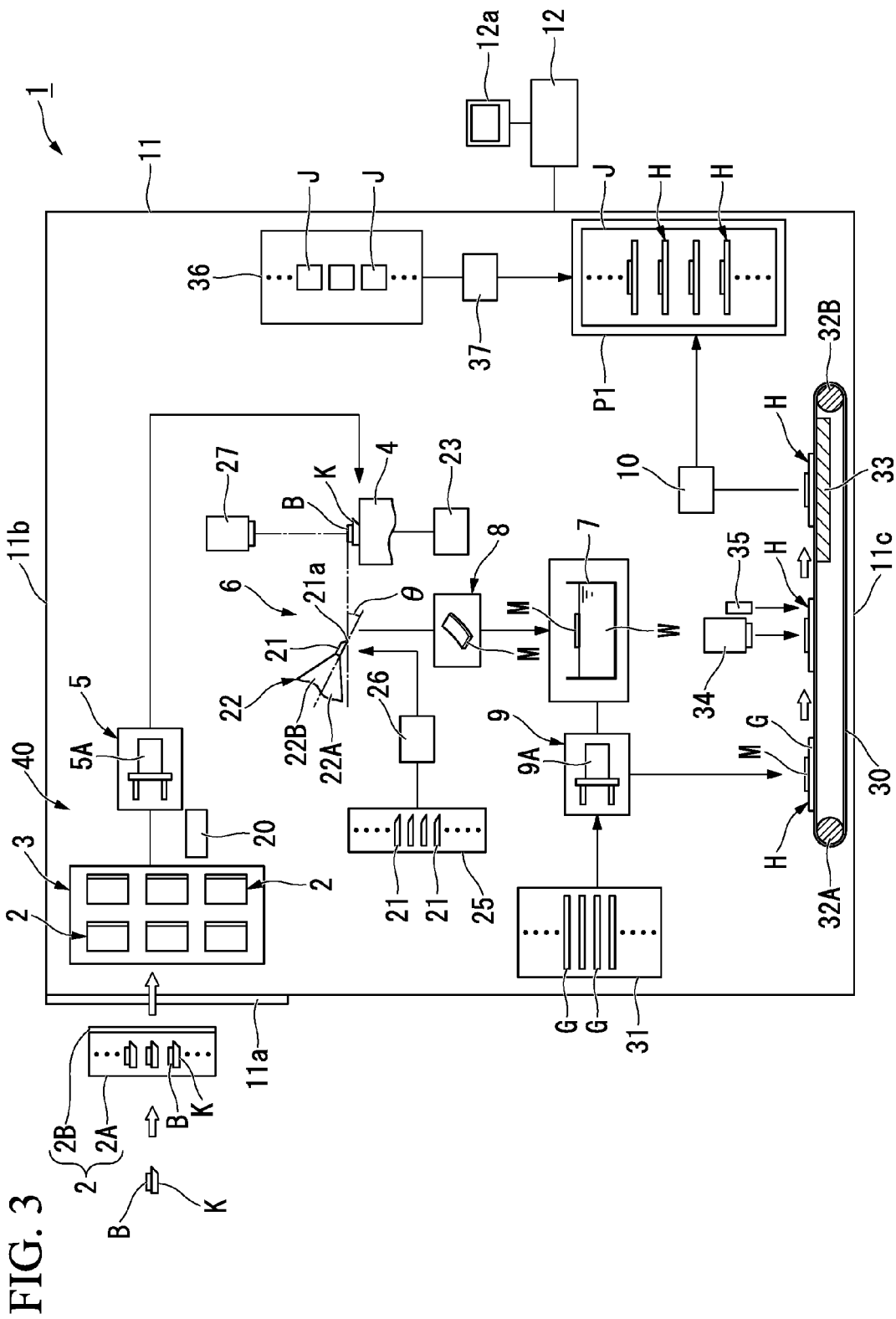
FIG. 3 is a schematic configuration view showing an embodiment of the automatic thin-cutting device according to the present invention.

As shown in FIG. 3, the automatic thin-cutting device 1 mainly includes: a plurality of magazines 2 in which the plurality of embedding blocks B are accommodated to be inserted into or removed from the magazines; a carousel (magazine holding portion) 3 which can detachably mount the magazines 2 individually; a block transport mechanism 5 which inserts or removes one embedding block B selected from the plurality of embedding block B accommodated in the magazine 2 mounted on the carousel 3 and places the embedding block on a stage 4 which is a thin-cutting position; a thin-cutting mechanism 6 which cuts the embedding block B placed on the stage 4 at a predetermined thickness and in which the cutting of thin section M is performed; a thin section transport mechanism (transport mechanism) 8 which transports the thin section M cut by the thin-cutting mechanism 6 to the storage tank 7 and floats the thin section M on a liquid surface to spread the thin section M; a slide glass handling mechanism (substrate disposition mechanism) 9 which scoops the spread thin section M from the liquid surface onto the slide glass G and prepares the thin section sample H; a slide glass accommodation mechanism 10 which accommodates the prepared thin section sample H in a basket J; a device case (housing) 11 which accommodates the components in the inner portion; and a control portion 12 which totally controls the components.

(Device Case)

The inner portion of the above-described device case 11 can be sealed, and for example, in the inner portion, an environmental condition such as humidity, temperature, or the like can be set to a desired condition. An access door 11a which is opened and closed by an operator is provided on the wall surface of the device case 11. The access door 11a is a door which is used when the magazine 2 is mounted or extracted, and by opening the access door 11a, access to the carousel 3 on which the magazine 2 is mounted is possible.

Moreover, in the present embodiment, a top surface 11b side of the device case 11 is defined as an upper side, a bottom surface 11c side is defined as a lower side, and a direction perpendicular to the top surface 11b and the bottom surface 11c is defined as a vertical direction.

(Magazine)

The magazine 2 is an accommodation case in which the entirety is formed in a vertically long rectangular parallelepiped shape, and can accommodate the plurality of embedding blocks B fixed to the cassettes K in a state where the embedding blocks B are arranged in one row along the vertical direction. The magazine 2 mainly includes a box-shaped magazine main body 2A in which the front surface is opened, and an opening and closing door 2B which is fixed to the magazine main body 2A.

When the opening and closing door 2B is closed, a portion of the plurality of embedding blocks B accommodated in the magazine main body 2A is covered, and thus, dropping of the embedding block B is prevented. Accordingly, the operator can deliver the magazine 2 at ease without paying attention to the dropping of the embedding block B.

(Carousel)

The magazine 2 configured as described above can be detachably mounted on the carousel 3. In the illustrated example, 6 magazines 2 are simultaneously mounted on the carousel 3.

The carousel 3 is disposed at a position at which access is possible from the outside by opening the access door 11a of the device case 11. Accordingly, the magazine 2 can be mounted on the carousel 3 or removed from the carousel 3 manually by the operator.

In addition, the carousel 3 can rotate about a rotation axis O extending in the vertical direction, moves the magazine 2 mounted by the rotation in a circumferential direction, and can set one selected magazine 2 to a block extraction position P2 (refer to FIG. 6) at which the magazine 2 faces the block transport mechanism 5.

Moreover, the operation of the carousel 3 is controlled by the control portion 12. In addition, in FIG. 3, the illustration of the carousel 3 is simplified.

(Reading Portion)

In addition, a reading portion 20 is disposed at a position adjacent to the carousel 3, and the reading portion 20 reads ID data printed on the cassette K of each embedding block B which is accommodated in the magazine 2 set at the block extraction position P2.

For example, the reading portion 20 and the magazine 2 positioned at the block extraction position P2 are movable relative to each other in a vertical direction, and according to this relative movement, the reading portion 20 can read the ID data printed on the cassette K of all embedding blocks B accommodated in the magazine 2. In addition, the reading portion 20 optically reads the ID data and outputs the read ID data to the control portion 12.

In addition, the plurality of magazines 2, the carousel 3, and the reading portion 20 function as a block storage device 40 which stores the plurality of embedding blocks B.

(Block Transport Mechanism)

The block transport mechanism 5 is a handling robot which includes a hand portion 5A capable of holding the cassette K which fixes the embedding block B, and is disposed at the position adjacent to the carousel 3. Based on the instruction from the control portion 12, the block transport mechanism 5 holds one embedding block B, which is accommodated in the magazine 2 set at the block extraction position P2 among the magazines 2 mounted on the carousel 3, by the hand portion 5A, can insert or remove the held embedding block B from the magazine 2, or can place the embedding block on the stage 4.

(Stage)

In the stage 4, an actuator or the like is incorporated into the inner portion, and the stage 4 is configured to appropriately move vertically based on the instruction from the control portion 12. Accordingly, it is possible to adjust the height of the embedding block B placed on the stage 4, and it is possible to thinly cut the embedding block B at a desired thickness (for example, 5 μm).

In addition, the stage 4 is a multi-axial stage in which rotation about the vertical axis and swing about a horizontal axis (two axes) can be performed. Therefore, the stage 4 freely controls the posture of the embedding block B and can set the direction, the inclination, or the like of the embedding block B to a desired state.

(Thin-Cutting Mechanism)

The thin-cutting mechanism 6 includes a cutting blade 21 which is disposed in the vicinity of the stage 4, a holder 22 which holds the cutting blade 21 in an exchangeable manner, and a moving mechanism 23 which moves the stage 4 with respect to the cutting blade 21 and thinly cuts the embedding block B by the cutting blade 21.

The cutting blade 21 is a long blade in which one end side becomes a blade edge 21a and is obliquely held (clamp-fixed) to the holder 22 with a predetermined drawing and rake angle θ. In addition, in the illustrated example, the blade edge 21a is a single edge. However, the blade edge may be a double edge.

The holder 22 mainly includes a placing plate 22A on which the cutting blade 21 is placed in a state where the blade edge 21a is exposed to the outside, and a pressing plate 22B which presses the placed cutting blade 21 to the placing plate 22A and in which the cutting blade 21 is clamp-fixed.

The moving mechanism 23 includes a guide rail (not shown) and a driving portion (not shown) which reciprocates the stage 4 along the guide rail at a predetermined speed, thinly cuts the embedding block B by the cutting blade 21 clamp-fixed by the holder 22 by reciprocating the stage 4 based on the instruction from the control portion 12, and performs the cutting of the thin section M.

In addition, the stage 4 raises the embedding block B by a predetermined amount according to the reciprocation by the moving mechanism 23. Accordingly, the embedding block B is cut at a predetermined thickness, and it is possible to prepare the thin section M.

In addition, in the present embodiment, the moving mechanism 23 is configured so that the stage 4 side moves with respect to the cutting blade 21. However, the moving mechanism 23 may be configured so that the cutting blade 21 side moves with respect to the stage 4, or may be configured so that the holder 22 side and the stage 4 side move together.

In either case, the moving mechanism 23 may be designed in any manner as long as the embedding block B and the cutting blade 21 move relative to each other and the thin-cutting can be performed by the cutting blade 21.

(Accommodation Case and Cutting Blade Transport Mechanism)

A plurality of the cutting blades 21 are accommodated in the accommodation case 25 in a state of being overlapped in multi stages, and after the cutting blades 21 are extracted one by one as necessary by the cutting blade transport mechanism 26, the cutting blade 21 is transported to the holder 22 and clamp-fixed. That is, the cutting blade 21 can be replaced at a predetermined timing.

Based on the instruction from the control portion 12, the cutting blade transport mechanism 26 inserts a new cutting blade 21 extracted from the accommodation case 25 into a portion between the placing plate 22A and the pressing plate 22B in the holder 22, and extrudes and transports the used cutting blade 21 from the holder 22.

Accordingly, the replacement of the cutting blade 21 is performed, and the pressing plate 22B of the holder 22 receives the intention that a new cutting blade 21 is set and is operated to perform the clamp-fixing of the new cutting blade 21 according to the instruction of the control portion 12.

In addition, the used cutting blade 21 extruded from the holder 22 is sent to a waste bottle (not shown) or the like via a waste chute (not shown) or the like.

(First Imaging Camera)

A first imaging camera 27 which images the embedding block B placed on the stage 4 is disposed above the stage 4. The first imaging camera 27 images the embedding block B which is illuminated by illumination light from a light source (not shown). In this case, the first imaging camera 27 can image the surface state or the internal state of the embedding block B according to the kind (for example, vertical illumination light or diffusion illumination light) of the illumination light.

In addition, the captured image is sent to the control portion 12, is recorded, and for example, is displayed on a monitor 12a connected to the control portion 12.

(Thin Section Transport Mechanism)

Based on the instruction from the control portion 12, the thin section transport mechanism 8 is a mechanism which transports the thin section M cut by the thin-cutting mechanism 6 up to the storage tank 7 and floats the thin section M on the liquid surface, and for example, the thin section transport mechanism 8 may transport the thin section using a transport belt, a transport tape, or the like, or may transport the thin section using a robotic hand, or the like.

(Storage Tank)

A liquid W such as water which is adjusted to a predetermined temperature is stored in the storage tank 7, and the thin section M floated on the liquid surface is spread by the liquid using a surface tension. In addition, the stored liquid W is discharged from the storage tank 7 via a circulation pipeline (not shown) as necessary and is supplied into the storage tank 7. Accordingly, a clear liquid W is stored in the storage tank 7 at all times.

(Slide Glass Handling Mechanism)

The slide glass handling mechanism 9 is a handling robot which includes the hand portion 9A capable of holding the slide glass G, and is disposed at a position adjacent to the storage tank 7. The slide glass handling mechanism 9 is operated based on the instruction from the control portion 12 and scoops the spread thin section M floated on the liquid surface on the slide glass G held by the hand portion 9A to transfer the thin section M, and thus, it is possible to prepare the thin section sample H.

After the slide glass handling mechanism 9 scoops the thin section M on the slide glass G and prepares the thin section sample H, the slide glass handling mechanism 9 delivers the thin section sample H onto a sample transport belt 30. Thereafter, the slide glass handling mechanism 9 holds a new slide glass G among the slide glasses G accommodated in a slide glass accommodation portion 31 and moves the new slide glass G to a standby state for scooping the next thin section M.

The slide glass accommodation portion 31 is disposed in the vicinity of the storage tank 7, and for example, several dozen to several hundred unused slide glasses G are accommodated in the inner portion of the slide glass accommodation portion 31.

(Sample Transport Belt and Hot Plate)

For example, the above-described sample transport belt 30 is an endless belt which is wound between a driving pulley 32A which is driven based on the instruction from the control portion 12 and a driven pulley 32B and can transport the thin section sample H to the downstream side by driving of the driving pulley 32A.

The hot plate 33 which is heated to a predetermined temperature is disposed on the downstream side of the sample transport belt 30, and the hot plate heats the thin section sample H placed on the sample transport belt 30 in a state where the thin section sample H is interposed between the hot plate 33 and the sample transport belt 30. Accordingly, superfluous liquid W remaining on the thin section sample H can be removed by vaporization, and it is possible to further spread the thin section M while preventing the existence of the liquid W between the slide glass G and the thin section M.

(Second Imaging Camera and Recording Portion)

In the present embodiment, while the thin section sample H is transported up to the downstream side on which the hot plate 33 is disposed by the sample transport belt 30, the imaging of the thin-cutting state in the thin section M using a second imaging camera 34 and the printing of individual data to the slide glass G using a recording portion 35 are performed.

The second imaging camera 34 is disposed above the sample transport belt 30, images the thin section M until the thin section sample H placed on the sample transport belt 30 is transported to the downstream side, and sends the captured image to the control portion 12. The captured image of the second imaging camera 34 sent to the control portion 12 is recorded in the control portion 12, and for example, is displayed on the monitor 12a.

For example, the recording portion 35 is a laser marker and is disposed to be adjacent to the second imaging camera 34, and based on the instruction from the control portion 12, the recording portion 35 irradiates the slide glass G with laser light and performs the printing of the individual data. In this case, similar to the second imaging camera 34, the recording portion 35 performs the printing until the thin section sample H is transported to the downstream side.

(Slide Glass Accommodation Mechanism)

The slide glass accommodation mechanism 10 is disposed above the sample transport belt 30 and is a mechanism which accommodates the thin section sample H on the sample transport belt 30 heated by the hot plate 33 in the basket J, based on the instruction from the control portion 12. For example, as this mechanism, the thin section sample H is extruded from the sample transport belt 30 using an extrusion rod driven by a cylinder or the like and may be stored in the basket J, or the thin section sample H may be accommodated in the basket J using a robotic hand or the like.

(Basket)

For example, the basket J is a dye basket and can accommodate several thin section samples H to several dozen thin section samples H at once, and the plurality of baskets J are stored in a basket accommodation portion 36 in advance. After the baskets J accommodated in the basket accommodation portion 36 are sequentially extracted by a basket supply mechanism 37 which is operated based on the instruction from the control portion 12, the baskets J are set at a sample accommodation position P1. At the sample accommodation position P1, the thin section samples H are accommodated in the basket J.

When the thin section samples H having the predetermined number of sheets are accommodated in the basket J, the basket J is sent into a storage cabinet (not shown) so as to be stored. In this case, warm wind adjusted to a predetermined temperature circulates through the storage cabinet, and thus, the thin section samples H are dried at an optimal state.

(Block Storage Device)

Next, among the components, the configuration of the block storage device 40 will be described in detail.

As described above, the block storage device 40 includes the plurality of magazines 2, the carousel 3 which detachably holds each of the plurality of magazine 2, and the reading portion 20 which is disposed to be adjacent to the carousel 3 and reads the ID data attached to the cassette K.

(Magazine)

First, the magazine 2 will be described in detail.

Figure 4:
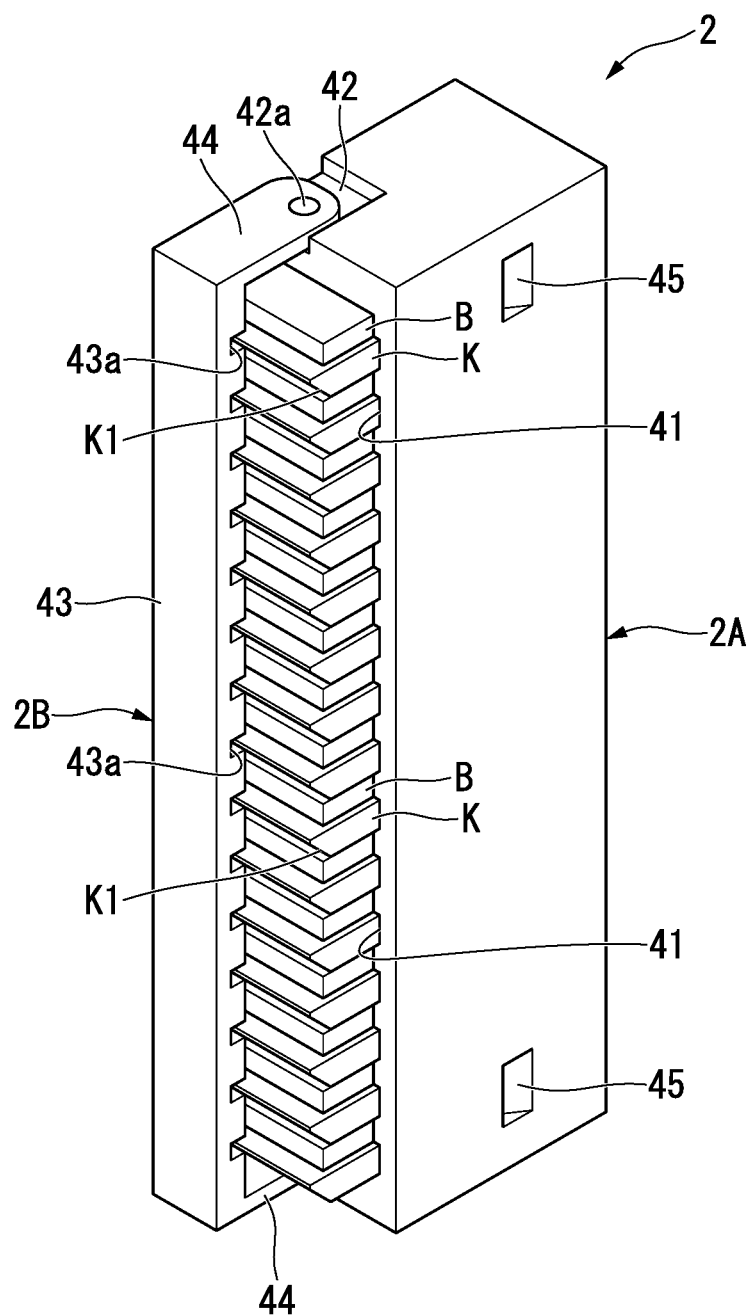
FIG. 4 is a perspective view of a magazine shown in FIG. 3.
Figure 5:
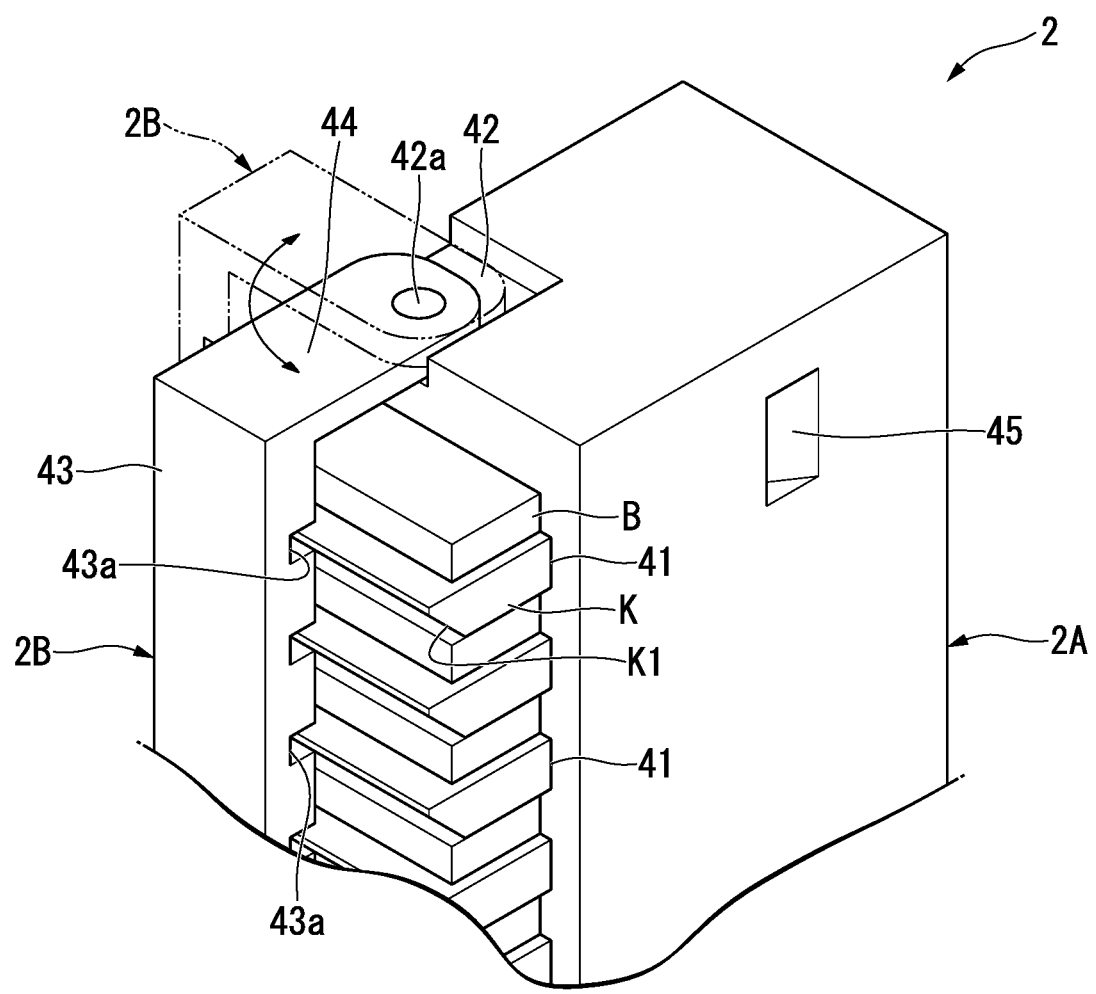
FIG. 5 is a partially enlarged view of the magazine shown in FIG. 4.

As shown in FIGS. 4 and 5, the magazine 2 mainly includes the magazine main body 2A in which the front surface is opened, and the opening and closing door 2B which is fixed to the magazine main body 2A.

A guide groove 41 which guides the cassette K is formed inside two side wall portions of the magazine main body 2A to be opposite to the right and the left from the front surface side toward the rear surface side. Accordingly, the cassette K is inserted to be introduced from the front surface side, and the embedding block B can be accommodated in the magazine main body 2A. In addition, the plurality of guide grooves 41 are formed at constant intervals in the vertical direction. Therefore, it is possible to accommodate the plurality of embedding blocks B in the state where the embedding blocks B are arranged in one row along the vertical direction.

In addition, the size of the magazine main body 2A is designed so that the cassette K and the embedding block B slightly protrude to the front surface side, that is, the depth of the magazine main body 2A is shorter than that of the cassette K.

A step portion 42 which is depressed on the portion, which is positioned on the front surface side, by one step further than other portions is formed on the top wall portion and the bottom wall portion of the magazine main body 2A, and the opening and closing door 2B is attached to the magazine main body 2A using the step portion 42.

The opening and closing door 2B includes a door main body 43 having the same length as that of the magazine main body 2A, and bent pieces 44C which extend to the upper end portion and the lower end portion of the door main body 43 and overlap with the step portion 42, and is formed in a C shape in a side view.

A rotary shaft 42a, in which the axial direction is along the vertical direction, is fixed to the step portion 42. Moreover, the bent pieces 44 overlap with the step portions 42 in the state where the bent pieces 44 are rotatably fixed to the rotary shaft 42a. Accordingly, the opening and closing door 2B can be opened and closed between a closing state in which the door main body 43 covers the front surface side of the magazine main body 2A, and an opening state in which the door main body 43 is rotated by 90° about the rotary shaft 42a from the closing state and the front side is opened.

During the closing state, the door main body 43 covers a portion of the cassettes K which slightly protrudes from the front side of the magazine main body 2A, and thus, dropping of the embedding block B is prevented. In this case, in the door main body 43, a notch 43a into which a portion of the inclined surface K1 in the cassette K is fitted is formed in accordance with the interval of the cassette K in the vertical direction. Accordingly, rattling of the cassette K in the close state is prevented.

Moreover, engagement concave portions 45 which engage with engagement claws 61a of holding hands 61 described below are formed on portions close to the top wall portion and the bottom wall portion outside the side wall portion of the magazine main body 2A. The engagement claws 61a engage with the engagement concave portions 45, and thus, the magazine 2 is held by the carousel 3.

(Carousel)

Subsequently, the carousel 3 will be described in detail.

Figure 6:
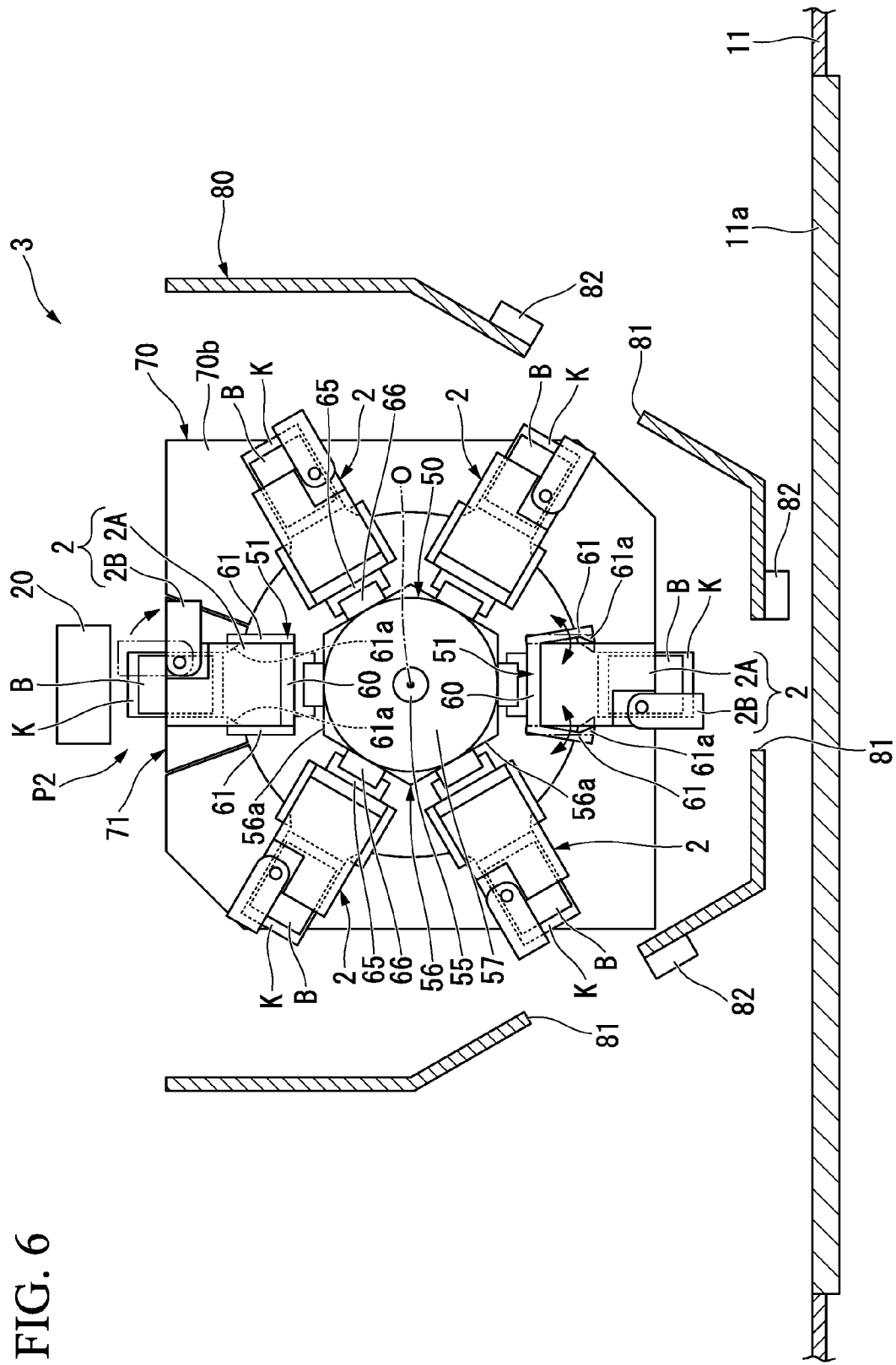
FIG. 6 is a top view of a carousel configuring an embedding block storage device shown in FIG. 3.
Figure 7:
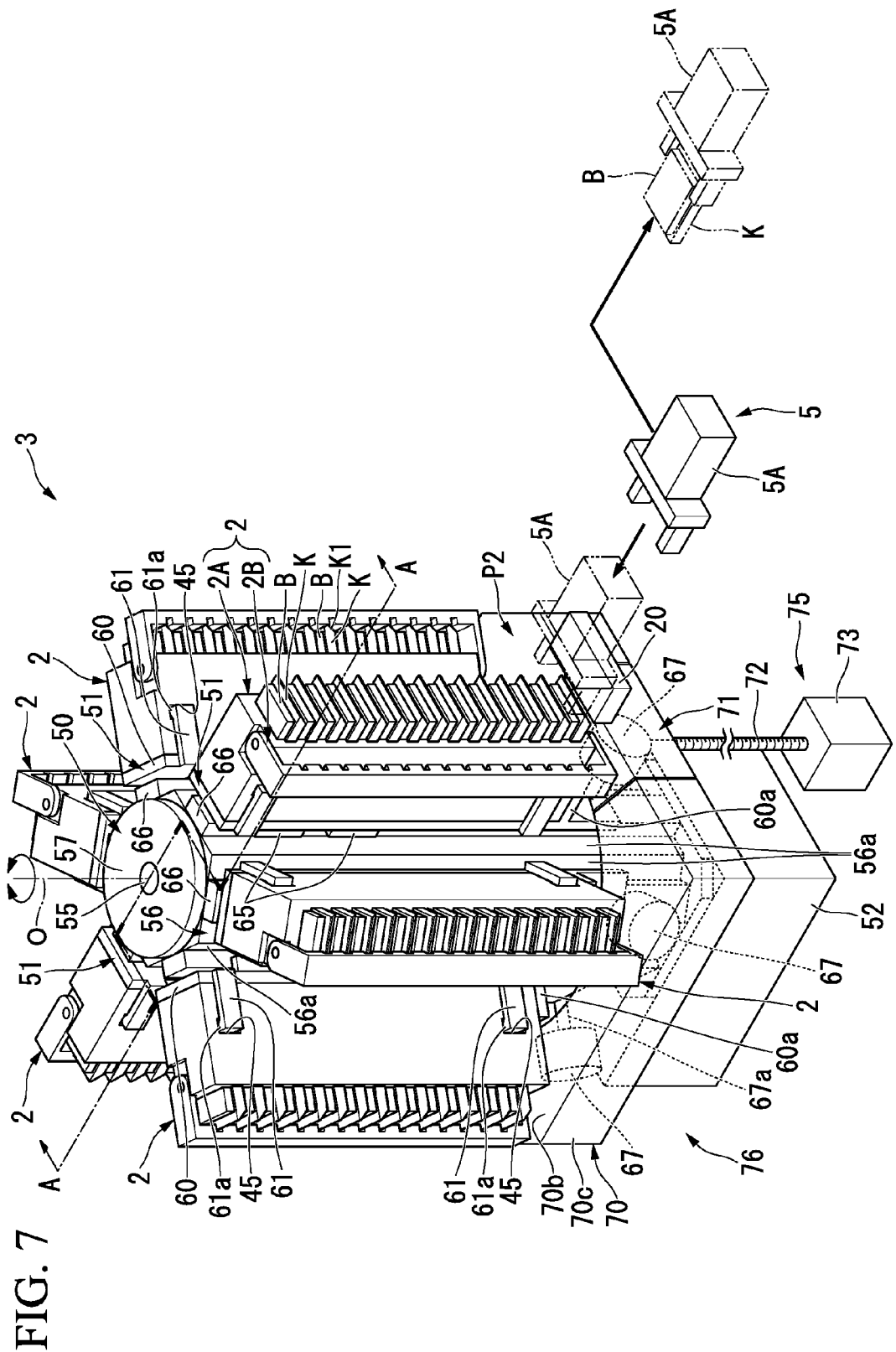
FIG. 7 is a perspective view of the carousel shown in FIG. 6.
Figure 8:
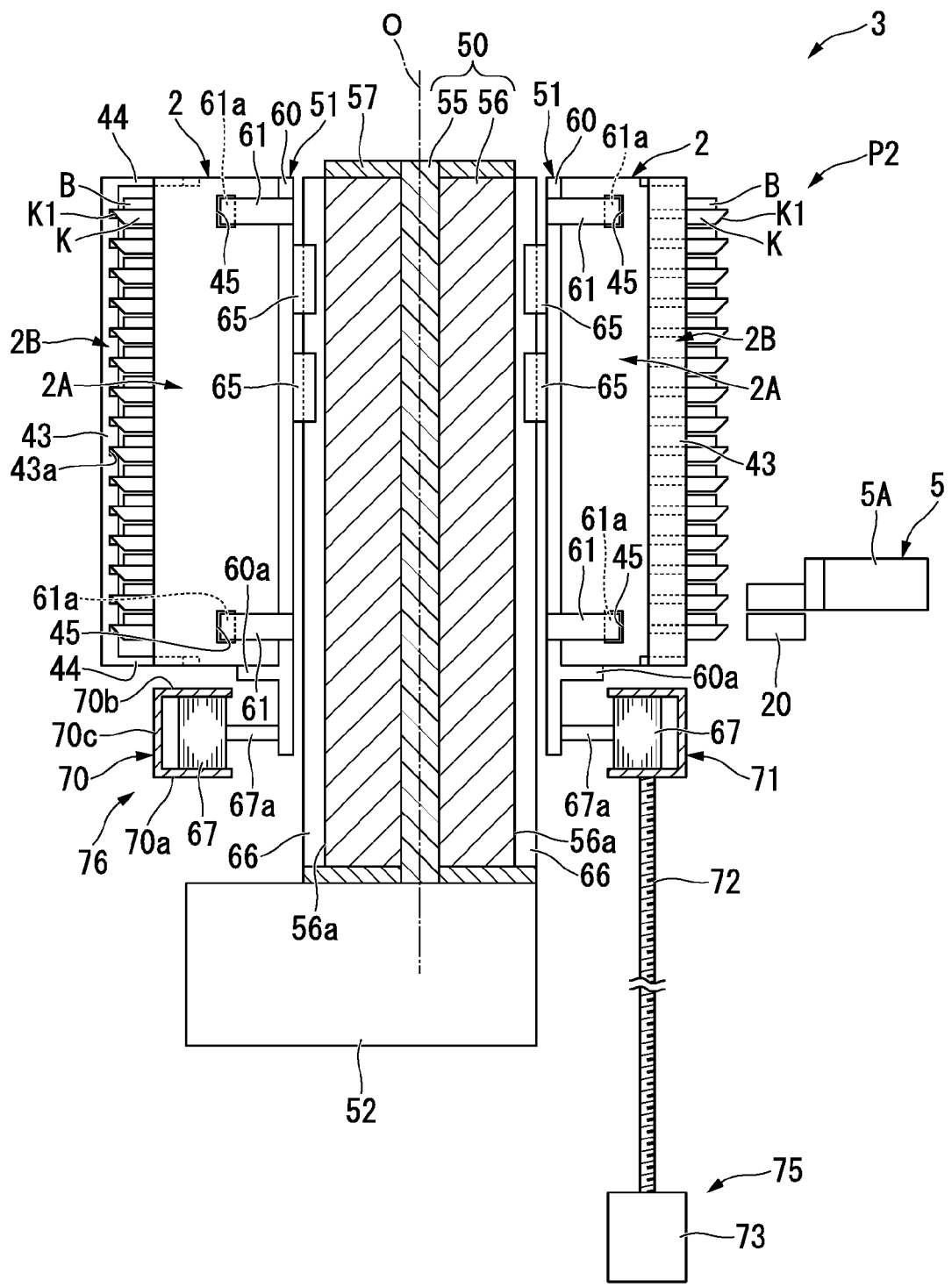
FIG. 8 is a cross-sectional view taken along arrow A-A of the carousel shown in FIG. 7.
Figure 9:
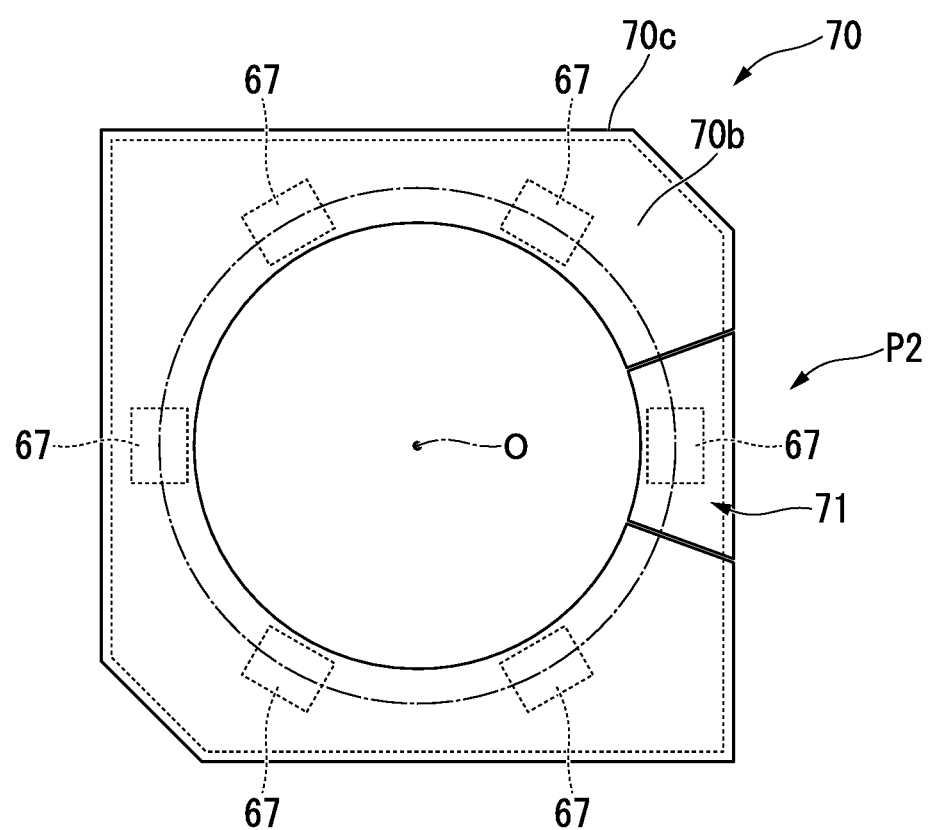
FIG. 9 is a top view of a fixing table configuring the carousel shown in FIG. 8.

As shown in FIGS. 6 to 8, the carousel 3 is disposed at the position adjacent to the access door 11a in the device case 11, and the carousel 3 includes a rotary block (rotary body) 50 which is rotatable about a rotation axis O extending in the vertical direction, holding mechanisms 51 which are multiply provided at intervals along the circumferential direction of a circumferential wall portion 56a in the rotary block 50 and which detachably hold six magazines 2 individually, and a driving motor (rotational drive) 52 which moves the six magazines 2 held by the holding mechanisms 51 in the circumferential direction by rotating the rotary block 50 and which positions one of the magazines 2 at a block extraction position P2 facing the reading portion 20.

The rotary block 50 includes a rotary shaft portion 55 which extends along the vertical direction, includes a lower end portion connected to an output shaft (not shown) of the driving motor 52, and is rotated about the rotation axis O according to the driving of the driving motor 52, and a block main body 56 which is integrally fixed to the rotary shaft portion 55 to surround the rotary shaft portion 55 from the outside in the radial direction.

The block main body 56 is formed in a hexagonal column shape extending in the vertical direction, and includes six circumferential wall portions 56a. The block main body 56 is rotatable about the rotation axis O along with the rotary shaft portion 55. Moreover, the upper end portion of the rotary shaft portion 55 protrudes further upward than the upper end portion of the block main body 56, and a fixing disk 57 which covers the block main body 56 from the above is attached to the protruded portion.

In addition, the entire length along the vertical direction in the block main body 56 is longer than the length of the magazine 2.

The operation of the driving motor 52 is controlled by the control portion 12, and for example, intermittently rotates the rotary shaft portion 55 in a constant direction based on the instruction from the control portion 12. Accordingly, for example, it is possible to set the six magazines 2 to the block extraction position P2 in order.

In addition, the driving motor 52 is fixed to the device case 11 using a frame (not shown).

The holding mechanism 51 includes a holding plate 60 and a pair of holding hands 61 attached to the holding plate 60.

The holding plate 60 is attached to each circumferential wall portion 56a of the block main body 56 via a slider 65 and a guide rail 66. The width of the holding plate 60 is the same as the width of the magazine main body 2A and is a vertically long plate having a longer length than that of the magazine main body 2A. Moreover, in the holding plate 60, a magazine support 60a which supports the magazine 2 from the lower portion toward the outside in the radial direction protrudes.

Accordingly, it is possible to place the magazine main body 2A on the magazine support 60a, and thus, the position in the vertical direction of the magazine 2 with respect to the holding plate 60 is positioned. Moreover, when the magazine main body 2A is placed on the magazine support 60a, the entirety of the rear surface of the magazine main body 2A comes into surface-contact with the holding plate 60.

The pair of holding hands 61 are disposed at the position positioned on the upper end portion side of the holding plate 60 and a portion positioned above the magazine support 60a to correspond the engagement concave portions 45 in the magazine 2 placed on the magazine support 60a.

The engagement claw 61a which engages with the engagement concave portion 45 formed on the magazine main body 2A is formed on the tip portion of each of the pair of holding hands 61. Moreover, in the pair of holding hands 61, the bases portions thereof are positioned on the surfaces of the holding plate 60, the tips portion are disposed to be positioned outside in the radial direction from the holding plate 60, and the base portions are rotatably attached to the holding plate 60 so that the engagement claws 61a can approach or separate from each other (FIG. 6).

In this case, a biasing member (not shown) such as a plate spring is interposed between the holding hand 61 and the holding plate 60, and the pair of holding hands 61 are biased at all times so that the engagement claws 61a approach each other.

Accordingly, by placing the magazine main body 2A on the magazine support 60a, the engagement claws 61a of the pair of holding hands 61 are spontaneously inserted into the engagement concave portions 45 of the magazine main body 2A and engage with the engagement concave portions 45, and thus, it possible to hold the magazine 2.

In addition, by separating the magazine 2 from the holding plate 60 against the biasing force of the holding hand 61, the engagement claws 61a are separated from the engagement concave portions 45, and it is possible to remove the magazine 2.

Moreover, a roller shaft 67a protrudes toward the outside in the radial direction on the lower end side of the holding plate 60, and a roller 67 is rotatably supported by the protruded end portion of the roller shaft 67a.

The holding mechanism 51 configured as described above is fixed to the block main body 56 via the slider 65 and the guide rail 66.

The guide rail 66 is a long rail which extends in the vertical direction, and is attached to the circumferential wall portion 56a of the block main body 56. In this case, the guide rail 66 is attached over the entire length of each circumferential wall portion 56a.

The slider 65 is a movable element which is attached so as to be movable along the guide rail 66, and in the shown example, two sliders are provided at slight intervals in the vertical direction with respect to the guide rail 66. Moreover, the holding plate 60 is fixed to the two sliders 65. Accordingly, each holding mechanism 51 is movable in the vertical direction with respect to the rotary block 50.

In addition, an annular fixing table 70 along which the rollers 67 travel is disposed between the plurality of magazines 2 and the driving motor 52.

As shown in FIGS. 6 to 9, the fixing table 70 includes an annular bottom plate 70a, an annular top plate 70b, and an outer plate 70c which is continuously provided between the radially outer edges of the bottom plate 70a and the top plate 70b, is formed in a C shape in a cross-sectional view opened to the rotary block 50 side, and is formed in an annular shape which surrounds the rotary block 50 from the outside in the radial direction.

Moreover, the fixing table 70 is positioned outside in the radial direction of the magazine support 60a of each holding plate 60, and when each holding plate 60 moves in the vertical direction, the fixing table 70 is designed so that the fixing table 70 and the magazine support 60a do not interfere with each other.

In addition, the roller 67 is disposed so as to travel between the bottom plate 70a and the top plate 70b in the fixing table 70. Accordingly, when the holding mechanism 51 moves in the circumferential direction by the rotation of the rotary block 50, the roller 67 can travel on the bottom plate 70a about the rotation axis O while being interposed between the bottom plate 70a and the top plate 70b.

Moreover, the fixing table 70 is divided at intervals in the circumferential direction at the block extraction position P2, and the divided portion functions as a lifting table 71.

The upper end side of a ball screw 72 which extends along the vertical direction is connected to the bottom plate 70a in the lifting table 71. In the ball screw 72, the rotation direction, the rotational speed, or the like is controlled by the driving portion 73 such as a motor which is operated based on the instruction of the control portion 12, and accordingly, the ball screw 72 is vertically moved.

Figure 10:
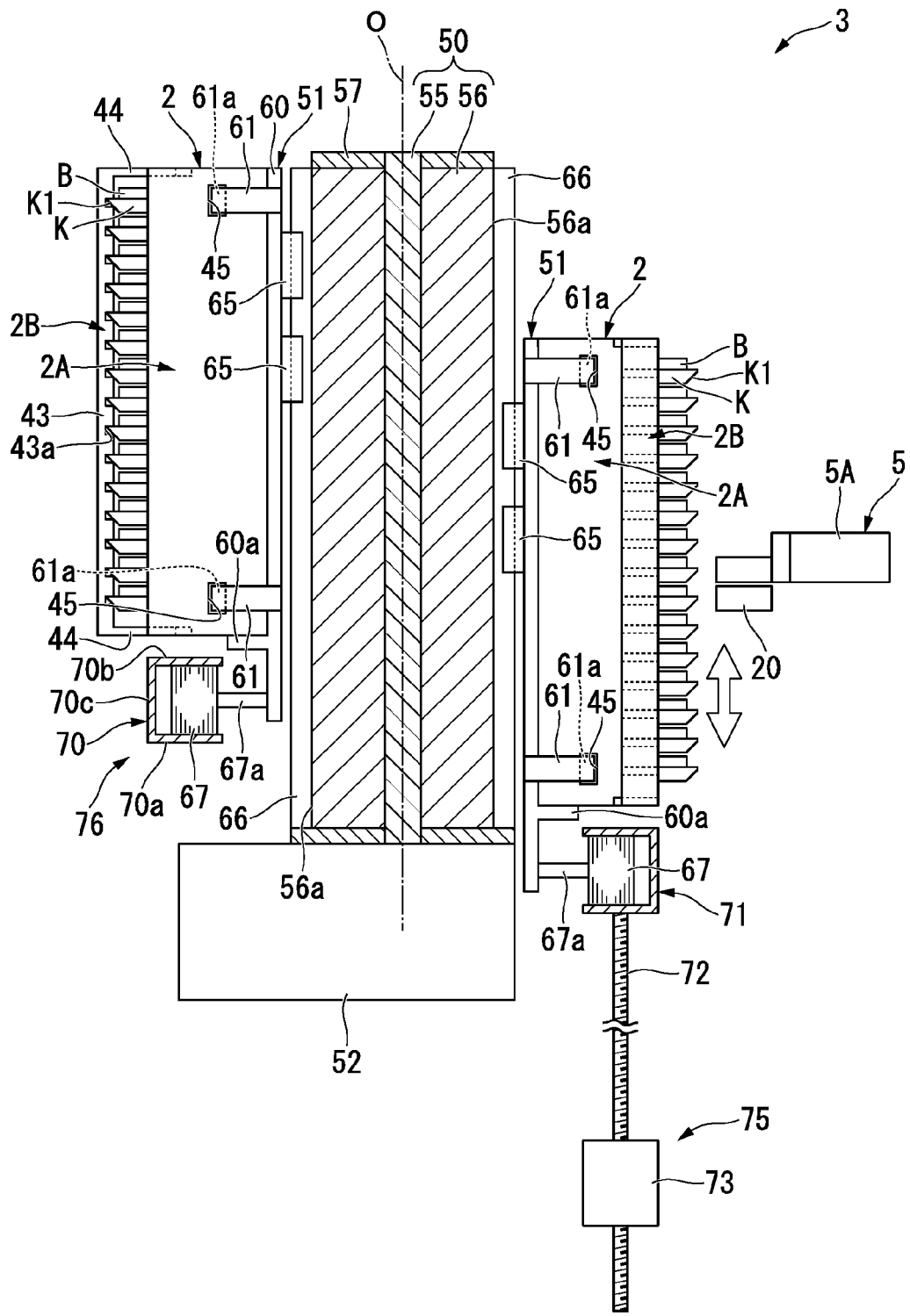
FIG. 10 is a view showing a state where the magazine set at a block extraction position is moved from the state shown in FIG. 8.

That is, as shown in FIG. 10, when the magazine 2 is set at the block extraction position P2 by the rotation of the rotary block 50, the ball screw 72 is vertically moved by the driving portion 73, and thus, it is possible to move the holding mechanism 51 holding the magazine 2 in the vertical direction.

The lifting table 71, the ball screw 72, and the driving portion 73 described above function as a lifting mechanism 75 which moves the holding mechanism 51 holding the magazine 2 positioned at the block extraction position P2 in the vertical direction.

In addition, since the rollers 67 are disposed between the bottom plate 70a and the top plate 70b in the fixing table 70, the remaining holding mechanisms 51 which hold the magazines 2 except for the magazine 2 positioned at the block extraction position P2 are not moved in the vertical direction.

Accordingly, the fixing table 70 and the roller 67 function as a regulation mechanism 76, which regulates the movement in the vertical direction, with respect to the holding mechanism 51 holding the magazines 2 except for the magazine 2 positioned at the block extraction position P2.

As shown in FIG. 6, the carousel 3 configured as described above is protected so that the periphery is covered by a protection cover 80.

The protection cover 80 covers the magazine 2, which is held by the rotary block 50 and the holding mechanism 51, from the outside in the radial direction. Specifically, the protection cover 80 covers the carousel 3 so that the carousel 3 is not exposed to the access door 11a side which is formed in the device case 11, and the protection cover is opened in the direction of the block extraction position P2. Accordingly, even when the access door 11a is opened, the carousel 3 is protected by the protection cover 80.

Moreover, in the protection cover 80, an opening portion 81 is formed at the positions corresponding to the magazines 2 except for the magazine 2 which is set at the block extraction position P2 in the plurality of magazines 2. Accordingly, it is possible to perform access from the access door 11a side with respect to the magazines 2 except for the magazine 2 set at the block extraction position P2, through the opening portion 81, and the magazines can be attached to and detached from the carousel 3.

In addition, in the illustrated example, the case where three opening portions 81a are formed on the protection cover 80 is described.

(Reading Portion)

As shown in FIGS. 6 and 7, the reading portion 20 is disposed in the outside in the radial direction from the lifting table 71 and is fixed in the state where a reading surface faces the embedding blocks B accommodated in the magazine 2 set at the block extraction position P2.

Moreover, as shown in FIG. 10, the lifting table 71 moves in the vertical direction by the vertical direction of the ball screw 72, the magazine 2 set at the block extraction position P2 and the reading portion 20 move relative to each other in the vertical direction, and thus, the reading portion 20 can read the ID data attached to the cassettes K of all embedding blocks B accommodated in the magazine 2.

<Operation of Automatic Thin-cutting Device>

Next, the operation of the automatic thin-cutting device 1 configured as described above will be described.

Moreover, in the present embodiment, first, the overall flow until the thin section sample H is prepared is simply described, and thereafter, the flow of the partial process will be described in detail.

First, as advance preparation, after the operator accommodates cassettes K, to which embedding blocks B are fixed, in the plurality of magazines 2, the operator opens the access door 11a of the device case 11, and mounts the magazines 2 on the carousel 3. After each magazine 2 is mounted on the carousel 3, the access door 11a is closed. In addition, the operator confirms whether or not the cutting blade 21 is appropriately set into the accommodation case 25, whether or not the slide glass G is appropriately set to the slide glass accommodation portion 31, whether or not the basket J is appropriately set to the basket accommodation portion 36, or the like, and thus, the advance preparation ends.

After the advance preparation ends, the operator starts the operation of each component in the device case 11 through the control portion 12.

Then, the control portion 12 sequentially rotates the carousels 3 and reads the ID data by the reading portion 20, and thereafter, the cassettes of the embedding blocks B subjected to the thin-cutting are held using the hand portions 5A by the block transport mechanism 5. Subsequently, after the held embedding block B is extracted from the magazine 2 by the block transport mechanism 5, the embedding block B is placed on the stage 4 via the cassette K.

When the setting operation of the embedding block B on the stage 4 ends, the control portion 12 starts the thin-cutting operation of the embedding block B.

First, the upper surface of the embedding block B is adjusted to a desired height position by adjusting the height of the stage 4. In addition, the moving mechanism 23 reciprocates the stage 4 in the thin-cutting mechanism 6, and thus, the embedding block B is thinly cut by the cutting blade 21 which is clamped-fixed by the holder 22. Accordingly, it is possible to perform rough-flattening of the embedding block B.

When the thin-cutting is performed, the first imaging camera 27 images the embedding block B. This captured image is recorded in the control portion 12 and is displayed on the monitor 12a. Accordingly, the operator can confirm the surface state or the internal state of the embedding block B by the captured image which is displayed on the monitor 12a. Moreover, with reference to the captured image, it is possible to incline or rotate an appropriate stage 4 during the thin-cutting. As a result, it is possible to expose an optimal surface to the surface by rough machining of the embedding block B.

In addition, when a flattening operation is performed by the above-described rough machining, the operation in which the thin section M is transported to the storage tank 7 by the thin section transport mechanism 8 is not performed. Accordingly, the thin section M generated in the case becomes cutting debris and is recovered to a recovery portion (not shown).

Subsequently, after the flattening of the embedding block B ends, the control portion 12 transfers the operation of the automatic thin-cutting device 1 from the rough machining operation to a main cutting operation. In this case, the control portion 12 operates the cutting blade transport mechanism 26, and replaces the cutting blade 21 used in the rough machining with a new cutting blade 21. Moreover, the replacement of the cutting blade 21 is not limited to this case, and may be appropriately performed as necessary.

When the operation is transferred to the main cutting operation, the control portion 12 prepares the thin section M by the thin-cutting mechanism 6, transports the prepared thin section M to the storage tank 7 by the thin section transport mechanism 8, and floats the thin section on the liquid surface. Accordingly, the thin section M is spread, and curling or the like generated during the thin-cutting is removed.

Subsequently, the control portion 12 operates the slide glass handling mechanism 9, scoops the thin section M floated on the liquid surface onto the slide glass G, and prepares the thin section sample H. The slide glass handling mechanism 9 places the prepared thin section sample H on the sample transport belt 30 and delivers the thin section sample H.

Moreover, the control portion 12 drives the driving pulley 32A, and transports the thin section sample H placed on the sample transport belt 30 toward the downstream side. Then, while the thin section sample H is transported to the hot plate 33, the second imaging camera 34 images the thin section M, and the captured image is sent to the control portion 12.

Based on the captured image received from the second imaging camera 34, the control portion 12 determines whether or not the thin section M subjected to the main cutting is appropriately cut thinly. Here, when the control portion 12 determines that the thin-cutting is good, the control portion 12 operates the recording portion 35, and the individual data associated with the ID data read from the cassette K is recorded in the slide glass G of the thin section sample H.

In addition, the thin section sample H in which the individual data is recorded is further transported to the downstream side of the sample transport belt 30 and is heated by the hot plate 33. Moreover, the control portion 12 operates the slide glass accommodation mechanism 10 and accommodates the heated thin section sample H in the basket J.

As the determination result with respect to the quality of thin-cutting, when the control portion 12 determines that the thin-cutting is not good, the control portion 12 does not operate the slide glass accommodation mechanism 10 and delivers the thin section sample H from the sample transport belt 30 to a defective product discharging chute (not shown). Accordingly, the thin section sample H which is the defective product is not accommodated in the basket J and is recovered.

When the thin section samples H which are determined as good products are accommodated in the basket J in a predetermined number, the basket J is sent to the storage cabinet and is stored, the basket supply mechanism 37 extracts a new basket J from the basket accommodation portion 36 and sets the new basket J at the sample accommodation position P1, and all subsequent accommodation operations are prepared.

As described above, according to the automatic thin-cutting device 1 of the present embodiment, not only the thin section M but also the thin section sample H is automatically prepared, and it is possible to accommodate the thin section samples H in the basket J in a predetermined number.

Accordingly, the operator can directly transfer the basket J to the dyeing process of the biological sample S by appropriately extracting the basket J from the storage cabinet, and then the basket J can be remarkably easily used. Particularly, since it is possible to collect the thin section samples H, in which the same dyeing operation is performed, in the same basket J, great convenience is obtained.

In addition, in the automatic thin-cutting device 1 of the present embodiment, since the block storage device 40 is provided, the following effects can be exerted.

That is, as shown in FIG. 6, when the access door 11a is closed, the control portion 12 operates the driving motor 52. Then, the driving motor 52 rotates the rotary block 50 about the rotation axis O and moves the six magazines 2 held by the holding mechanism 51 in the circumferential direction. Accordingly, it is possible to set one of the magazines 2 at the block extraction position P2.

Moreover, during the rotation of the rotary block 50, the roller 67 travels on the bottom plate 70a while being interposed between the bottom plate 70a and the top plate 70b in the fixing table 70, and thus, each holding mechanism 51 smoothly moves in only the circumferential direction without moving in the vertical direction. Moreover, as shown in FIG. 8, when the magazine 2 is set at the block extraction position P2, the roller 67 in the holding mechanism 51 holding the magazine 2 is moved to the lifting table 71. In addition, when the magazine 2 is set at the block extraction position 2, the opening and closing door 2B is spontaneously opened, or is rotated 90° by an opening mechanism (not shown) and opened.

When one of the magazines 2 is set at the block extraction position P2, the control portion 12 stops the driving motor 52, operates driving portion 73, and vertically moves the ball screw 72. Accordingly, as shown in FIG. 10, it is possible to move the holding mechanism 51 holding the magazine 2 set at the block extraction position P2 in the vertical direction, and thus, it is possible to move the magazine 2 and the fixed reading portion 20 relative to each other in the vertical direction.

According to this relative position, the reading portion 20 can read the ID data attached to the cassettes K of all embedding blocks B accommodated in the magazine 2. In this way, it is possible to effectively read the ID data of all the embedding blocks B in the magazine 2 in the state where the embedding blocks are accommodated in the magazine 2.

Meanwhile, the control portion 12 records the ID data received from the reading portion 20 in association with the position information of the embedding cassette K in the magazine 2. In addition, the recorded information is displayed on the monitor 12a, and for example, a flag of the recording completion is attached to the information.

Accordingly, the operator can rapidly confirm the ID data before the thin-cutting operation is performed. Moreover, when the embedding block B to be thinly cut is determined based on the ID data, the control portion 12 appropriately moves the ball screw 72 vertically, and a desired embedding block B is positioned at the position at which the embedding block opposes the hand portion 5A of the block transport mechanism 5. Accordingly, as shown in FIG. 7, it is possible to reliably extract the embedding block B from the inner portion of the magazine 2 using the hand portion 5A, and it is possible to transport the embedding block to the stage 4.

Moreover, after the thin-cutting ends, when the hand portion 5A of the block transport mechanism 5 returns the embedding block B into the magazine 2, the control portion 12 records the ending of the thin-cutting operation of the embedding block B in association with the ID data. Accordingly, it is possible to correctly understand whether or not the thin-cutting operations of all embedding blocks B in the magazine 2 end.

However, when the thin-cutting operation is not performed, the driving motor 52 stops, and the block transport mechanism 5 does not perform the access with respect to the magazines 2 except for the magazine 2 set at the block extraction position P2.

Accordingly, the operator can remove the magazine 2 in which the thin-cutting is completed in advance and which is positioned at the positions except for the block extraction position P2 from the holding mechanism 51 at an arbitrary timing. That is, after the access door 11a is opened, as shown in FIG. 6, it is possible to remove the magazine 2 from the holding mechanism 51 through the opening portion 81 of the protection cover 80. Therefore, it is possible to appropriately perform the recovery, the replacement, or the like of the embedding block B accommodated in the removed magazine 2.

Moreover, during this, it is possible to continuously perform the thin-cutting operation on the embedding blocks B accommodated in the magazine 2 set at the block extraction position P2 without being affected by the recovery, the replacement, or the like.

Therefore, according to the automatic thin-cutting device 1 of the present embodiment, it is possible to effectively perform the thin-cutting operation of the embedding block B. In addition, since the components are accommodated inside the device case 11, it is possible to prepare the thin section M having high quality without being easily affected by dust or the like.

Moreover, since the periphery of the carousel 3 is covered by the protection cover 80, it is possible to prevent the operator from coming into contact with the portions other than the magazine 2, and it is possible to obtain safety. Moreover, during the rotation of the rotary block 50, when the operator opens the access door 11a, the control portion 12 stops the driving motor 52. Accordingly, it is possible to prevent the operator from coming into contact with the carousel 3 and the magazine 2 during the rotation.

Moreover, in the above-described embodiment, preferably, when the thin-cutting operations of all embedding blocks B accommodated in each magazine 2 end, the control portion 12 informs of the intention.

For example, the information indicating the intention (such as the ending of all thin-cutting operations with respect to the magazine 2 currently positioned at the rotation position in the carousel 3) may be displayed on the monitor 12a. Moreover, as shown in FIG. 6, a completion display device 82 is provided in the vicinity of the opening portion 81 in the protection cover 80, and when the thin-cutting with respect to the magazine 2, which moves to the piston facing the opening portion 81, is completed, the intention may be displayed using the completion display device 82. As the display method, for example, a green lamp may be turned on or turned off, the color of the lamp may be changed from red to green, and the information such as "thin-cutting completion" may be displayed on a liquid crystal glass.

Accordingly, it is possible to prevent the operator from removing the magazine 2 in the state where the embedding blocks B which are not thinly cut remain.

Moreover, the technical scope of the present invention is limited to the above-described embodiment, and various modifications are applied to the above-described embodiment within a scope which does not depart from the gist of the present invention.

For example, in the above-described embodiment, the case where six magazines 2 are mounted on the carousel 3 is described. However, the number of the magazines 2 is not limited to the case. For example, the number of the magazines 2 which are simultaneously mounted on the carousel 3 may be set to an arbitrary number, for example, one, two, three, four, five, or seven or more.

Moreover, by fixing the reading portion 20 and moving the holding mechanism 51 holding the magazine 2 set at the block extraction position P2 in the vertical direction, the reading portion 20 and magazine 2 move relative to each other along the vertical direction. However, the movement direction of the magazine 2 with respect to the reading portion 20 may be the reverse direction. Accordingly, it is possible to effectively read the ID data and to improve throughput.

REFERENCE SIGNS LIST

B . . . embedding block, K . . . cassette, S . . . biological sample, P2 . . . block extraction position, 1 . . . automatic thin-cutting device, 2 . . . magazine, 3 . . . carousel (magazine holding portion), 5 . . . block transport mechanism, 6 . . . thin-cutting mechanism, 11 . . . device case (hosing), 12 . . . control portion, 20 . . . reading portion, 40 . . . block storage device, 50 . . . rotary block (rotary body), 51 . . . holding mechanism, 52 . . . driving motor (rotation drive portion), 75 . . . lifting mechanism, 76 . . . regulation mechanism, 80 . . . protection cover, 81 . . . opening portion of protection cover

What is claimed is:
1. A block storage device that stores an embedding block which includes an embedded biological sample and is held in a cassette to which ID data is attached in advance, the device comprising:
   a magazine configured to accommodate a plurality of the embedding blocks to be inserted into or removed from the magazine and to accommodate the embedding blocks in a state where the embedding blocks are arranged along a vertical direction in one row;
   a magazine holding portion configured to detachably hold each of a plurality of the magazines; and
   a reading portion configured to be disposed to be adjacent to the magazine holding portion and to read the ID data,
   wherein the magazine holding portion includes
   a rotary body configured to be rotatable around a rotation axis extended in a vertical direction,
   a holding mechanism configured to be multiply provided at intervals along a circumferential direction on a circumferential wall portion in the rotary body and to detachably hold the plurality of the magazines, and
   a rotation drive portion configured to move the plurality of the magazines held by the holding mechanism in the circumferential direction by rotating the rotary body and to position one of the magazines at a block extraction position facing the reading portion, wherein the magazine positioned at the block extraction position and the reading portion are movable relative to each other along the vertical direction.

2. The block storage device according to claim 1,
wherein a plurality of the holding mechanisms are movable in the vertical direction with respect to the rotary body,
wherein the magazine holding portion includes
a lifting mechanism configured to vertically move the holding mechanism which holds the magazine positioned at the block extraction position, among the plurality of the holding mechanisms, and
a regulation mechanism configured to regulate movements in the vertical direction of the remaining holding mechanisms which hold the magazines except for the magazine positioned at the block extraction position, among the plurality of the holding mechanisms while the holding mechanism which holds the magazine positioned at the block extraction position, among the plurality of the holding mechanisms, is vertically moved.

3. The block storage device according to claim 1, further comprising:
a protection cover configured to cover the periphery of the circumferential wall portion in the rotary body,
wherein an opening portion accessible to the magazine except for the magazine positioned at the block extraction position among the plurality of the magazines is formed on the protection cover.

4. The block storage device according to claim 1, further comprising:
a control portion configured to perform thin-cutting management of the embedding block based on the ID data read by the reading portion,
wherein when the control portion determines that the thin-cutting is completed with respect to all of the plurality of the embedding blocks accommodated in the magazine, the control portion informs of the fact.

5. An automatic thin-cutting device, comprising:
the block storage device according to claim 1;
a block transport mechanism configured to insert or remove one embedding block which is selected from the embedding blocks accommodated in the magazine positioned at the block extraction position into or from the magazine and to transport the embedding block to a thin-cutting position;
a thin-cutting mechanism configured to perform the thin-cutting on the embedding block set at the thin-cutting position and to cut a thin section; and
a housing configured to accommodate the components.

* * * * *